United States Patent
Choi et al.

(10) Patent No.: US 11,998,175 B2
(45) Date of Patent: Jun. 4, 2024

(54) MODULAR CAPSULE ENDOSCOPE RECONFIGURABLE IN DIGESTIVE ORGAN

(71) Applicants: INDUSTRY FOUNDATION OF CHONNAM NATIONAL UNIVERSITY, Gwangju (KR); KOREA INSTITUTE OF MEDICAL MICROROBOTICS, Gwangju (KR)

(72) Inventors: Eunpyo Choi, Gwangju (KR); Jongoh Park, Gyeonggi-do (KR); Chang-Sei Kim, Gwangju (KR); Byungjeon Kang, Gwangju (KR)

(73) Assignees: INDUSTRY FOUNDATION OF CHONNAM NATIONAL UNIVERSITY, Gwangju (KR); KOREA INSTITUTE OF MEDICAL MICROROBOTICS, Gwangju (KR)

( * ) Notice: Subject to any disclaimer, the term of this patent is extended or adjusted under 35 U.S.C. 154(b) by 564 days.

(21) Appl. No.: 17/286,894

(22) PCT Filed: Jan. 23, 2020

(86) PCT No.: PCT/KR2020/001188
§ 371 (c)(1),
(2) Date: Apr. 20, 2021

(87) PCT Pub. No.: WO2020/171403
PCT Pub. Date: Aug. 27, 2020

(65) Prior Publication Data
US 2021/0353135 A1    Nov. 18, 2021

(30) Foreign Application Priority Data
Feb. 19, 2019    (KR) .................... 10-2019-0019448

(51) Int. Cl.
A61B 1/00    (2006.01)
A61B 1/04    (2006.01)
(Continued)

(52) U.S. Cl.
CPC .......... *A61B 1/041* (2013.01); *A61B 1/00105* (2013.01); *A61B 1/00158* (2013.01);
(Continued)

(58) Field of Classification Search
CPC . A61B 1/041; A61B 1/00105; A61B 1/00158; A61B 1/00156; A61B 5/6861; A61B 2562/162
See application file for complete search history.

(56) References Cited

U.S. PATENT DOCUMENTS 9,198,563 B2 * 12/2015 Ferren .................... A61B 1/041
2014/0221741 A1 * 8/2014 Wang .................. A61B 1/2736
600/101

(Continued)

FOREIGN PATENT DOCUMENTS

CA    2840559 A1 *    1/2013    ......... A61B 1/00158
CN    108778092 A *    11/2018   ......... A61B 1/00016
(Continued)

OTHER PUBLICATIONS

Texas Gateway; "20.1 Magnetic Fields, Field Lines, and Force"; Oct. 16, 2017; <https://www.texasgateway.org/resource/201-magnetic-fields-field-lines-and-force> (Year: 2017).*

(Continued)

*Primary Examiner* — Timothy J Neal
(74) *Attorney, Agent, or Firm* — Harness, Dickey & Pierce, P.L.C.

(57) ABSTRACT

The present invention relates to a capsule-type endoscope assembly which can be assembled or disassembled in a digestive organ of an examinee, and a capsule-type endo-
(Continued)

scope system using the same. A capsule-type endoscope of the present invention can be actively operated by the application of an external magnetic field. In addition, according to the present invention, after an examinee has separately swallowed various diagnosis and treatment devices modularized according to a purpose of diagnosis and treatment, the diagnosis and treatment devices can be assembled in a digestive organ of the examinee. Therefore, a function of a capsule-type endoscope can be extended to various diagnosis and treatment areas conventionally covered by a conventional general endoscope.

9 Claims, 12 Drawing Sheets

(51) Int. Cl.
    *A61B 5/00*   (2006.01)
    *A61B 5/053*  (2021.01)
    *A61B 5/145*  (2006.01)
    *A61B 10/04*  (2006.01)

(52) U.S. Cl.
    CPC .......... *A61B 5/053* (2013.01); *A61B 5/14539* (2013.01); *A61B 5/4839* (2013.01); *A61B 10/04* (2013.01); *A61B 2562/0247* (2013.01)

(56) References Cited

U.S. PATENT DOCUMENTS

| | | | |
|---|---|---|---|
| 2017/0252141 A1* | 9/2017 | Alharmi | A61B 5/6874 |
| 2018/0168490 A1* | 6/2018 | Jones | A61B 5/7282 |

FOREIGN PATENT DOCUMENTS

| | | | | |
|---|---|---|---|---|
| DE | 102011005338 A1 * | 9/2012 | ............ | A61B 1/31 |
| JP | 2004-538055 A | 12/2004 | | |
| JP | 2007014634 A * | 1/2007 | ......... | A61B 1/00147 |
| JP | 2007-082816 A | 4/2007 | | |
| KR | 10-2014-0066372 A | 6/2014 | | |
| KR | 10-2018-0004001 A | 1/2018 | | |
| KR | 10-2018-0053852 A | 5/2018 | | |
| KR | 20180053852 A * | 5/2018 | ............ | A61N 7/00 |
| KR | 20190007309 * | 1/2019 | ............ | A61B 1/00 |

OTHER PUBLICATIONS

University of Birmingham; "Magnetic Materials: Soft Materials"; Feb. 28, 2003; <https://www.birmingham.ac.uk/Documents/college-eps/metallurgy/research/Magnetic-Materials-Background/Magnetic-Materials-Background-10-Soft-Magnets.pdf> (Year: 2003).*
International Search Report from corresponding PCT Application No. PCT/KR2020/001188, dated Sep. 11, 2020.

* cited by examiner

MODULAR CAPSULE ENDOSCOPE RECONFIGURABLE IN DIGESTIVE ORGAN

CROSS-REFERENCE TO RELATED APPLICATIONS

This application is a national phase application of PCT Application No. PCT/KR2020/001188, filed on Jan. 23, 2020, which claims priority to and benefit of Korean Patent Application No. 10-2019-0019448, filed on Feb. 19, 2019. The entire disclosures of the applications identified in this paragraph are incorporated herein by references.

TECHNICAL FIELD

The present disclosure was made with the support of the Ministry of Health and Welfare, Republic of Korea, under Project No. HI19C0642, which was conducted in the research project named "R&D Center for Practical Medical Microrobot Platform" in the research program titled "Korea Health Technology R&D Project" by the Korea Institute of Medical Microrobotics, under management of the Korea Health Industry Development Institute, from 12 Jun. 2019 to 31 Dec. 2022.

The present disclosure relates to a modular capsule endoscope reconfigurable in a digestive organ.

BACKGROUND ART

In recent years, the diseases of digestive organs are increasing in modern people due to lifestyle changes, such as a westernization of dietary habits and a lack of exercise. Thus, the utilization of endoscopes to prevent and treat digestive diseases is increasing. Typical cable endoscopes enter through the mouth or anus for the purpose of diagnosis of digestive organs. This causes pain to the patient and causes a risk for the side effects of anesthesia- or sleep-inducing drugs. Capsule endoscopes have been developed to remedy the shortcomings of such cable endoscopes. Capsule endoscopes are devices that can move along digestive organs by peristalsis of the digestive organs, photograph the inside of the human digestive organs, and transmit the photographed information to the outside through communication. Medical staff can determine the degrees of lesions inside the digestive organs through the information transmitted by the capsule endoscopes.

Conventional capsule endoscopes have made it difficult to attain accurate image diagnosis due to passive movement thereof, and allow only passive observation of the forward/backward regions of capsules without their own driving functions. Therefore, the desired sites are difficult to accurately photograph, and in particular, lesions in the regions with many curves cannot be properly observed. Moreover, a full day is required for capsule endoscopes to be inserted into and discharged from the body, and after discharge, a lot of analysis time is required for the medical staff to make a diagnosis using images stored in the capsule endoscopes. So, existing manual capsule endoscopes are restrictively applied to the small intestine to which typical endoscopes are difficult to apply. Recently, to overcome the limitations of conventional typical endoscopes and passive capsule endoscopes, research has been actively conducted to develop and commercialize an active capsule endoscope capable of photographing an image under the control of capsules using an external electromagnetic field.

Meanwhile, various types of devices are required for diagnosis and treatment of various diseases in the digestive organs. Conventional typical endoscopes, while having various types of devices inserted into channels inside, easily access lesion sites. On the other hand, despite having many advantages (active mobility, cleanness, high patient compliance, etc.), current active capsule endoscopes cannot load various types of devices due to the limited sizes thereof. Even if a device is loaded in a capsule, the capsule is difficult to swallow by mouth since the capsule is lengthened. Therefore, the use of active capsule endoscopes has been limited to the purpose of imaging diagnosis. Therefore, research to expand the functions of active capsule endoscopes by loading various diagnostic/treatment tools for, for example, tissue biopsy and drug delivery, in addition to imaging diagnosis of digestive organs, is also actively being conducted.

SUMMARY

Technical Problem

The present inventors conducted intensive research efforts to develop a capsule endoscope capable of being actively controlled in digestive organs and achieving various types of diagnosis and treatment in addition to imaging diagnosis. As a result, the present inventors implemented a modular reconfiguration mechanism whereby a device for diagnosis and treatment is modularized and the modules can be assembled or disassembled in the gastrointestinal tract, and thus completed the present disclosure.

Accordingly, an aspect of the present disclosure is to provide a capsule endoscope assembly capable of being assembled or disassembled in digestive organs of a subject.

Another aspect of the present disclosure is to provide a modular capsule endoscope assembly configured to enable diagnosis and treatment of various diseases in digestive organs.

Still another aspect of the present disclosure is to provide a capsule endoscope system including the capsule endoscope assembly and configured to be capable of being controlled more precisely.

Technical Solution

In accordance with an aspect of the present disclosure, there is provided a capsule endoscope assembly capable of being assembled or disassembled in a digestive organ of a subject, the capsule endoscope assembly including:

a capsule endoscope module having a camera at either one or both ends thereof to photograph the outside thereof;

a treatment module for treatment, diagnosis, or biopsy of a lesion site of the subject; and an interface module coupled to the capsule endoscope and the treatment module therebetween and including soft magnets.

In an embodiment of the present disclosure, the capsule endoscope module includes a permanent magnet.

In another embodiment of the present disclosure, the capsule endoscope assembly is assembled by attractive force between the modules, which are generated by the magnetization of the soft magnets included in the interface module when an external magnetic field is applied in parallel to an axial direction of the endoscope assembly.

In still another embodiment of the present disclosure, the capsule endoscope assembly is disassembled (i) by the elimination of the attractive force between the modules through the removal of the external magnetic field, or (ii) by the repulsive force between the modules, which is generated when an external magnetic field is applied in a direction vertical to the axial direction of the endoscope assembly.

In still another embodiment of the present disclosure, the material for the soft magnet may be a soft magnet selected from the group consisting of pure iron, electromagnetic soft iron, silicon steel, permalloy (Ni—Fe bases), Co—Fe-based alloys (ex. VACOFULX™), sendust (Fe—Al—Si bases), Mn—Zn-based ferrites, Ni—Zn-based ferrites, Fe-based amorphous alloys, Co-based amorphous alloys, Fe-based thin films and multilayer films, Co-based thin films and multilayer films, and Ni-based thin films and multilayer films, but is not limited thereto.

In still another embodiment of the present disclosure, the interface module has a hollow cylindrical shape. The interface module has a hollow cylindrical shape, and thus can prevent the field of view of the camera from being blocked even when the interface is coupled to the capsule endoscope.

In a specific embodiment of the present disclosure, the capsule endoscope assembly includes at least one capsule endoscope module, at least one interface module, and at least one treatment module.

In accordance with another aspect of the present disclosure, there is provided a capsule endoscope system including:

a capsule endoscope assembly including the capsule endoscope module, the treatment module, and the interface module;

a second capsule endoscope module having a camera at one end thereof to photograph the outside; and a fixing device including a permanent magnet and configured to fix the second capsule endoscope module onto the inner wall of a digestive organ outside the body of a subject.

Advantageous Effects

The present disclosure is directed to a capsule endoscope assembly capable of being assembled or disassembled in a digestive organ of a subject and a capsule endoscope system using the same. The capsule endoscope of the present disclosure can be actively controlled by the application of an external magnetic field. Furthermore, various diagnosis and treatment devices modulated according to the purpose of diagnosis and treatment can be assembled in a digestive organ of a subject after being swallowed by the subject. Therefore, the functions of the capsule endoscope can be extended to various diagnostic and treatment areas like typical endoscopes.

BEST MODE FOR CARRYING OUT THE INVENTION

A capsule endoscope assembly capable of being assembled or disassembled in a digestive organ of a subject, the capsule endoscope assembly including: a capsule endoscope module having a camera at either one or both ends thereof to photograph the outside; a treatment module for treatment, diagnosis, or biopsy of a lesion site of the subject; and an interface module coupled to the capsule endoscope and the treatment module there between and including soft magnets.

DETAILED DESCRIPTION

Hereinafter, embodiments of the present disclosure will be described with reference to accompanying drawings. The embodiments of the present disclosure are given for specifically illustrating the present disclosure, and the scope of the present disclosure is not limited thereto.

The present disclosure relates to a modularized capsule endoscope assembly and, more specifically, to an active capsule endoscope capable of implementing a module reconfiguration mechanism in which, instead of swallowing a modularized diagnosis or treatment device assembled in the capsule endoscope, respective modules can be assembled or disassembled in the gastrointestinal tract after being separately swallowed.

A basic capsule endoscope system is configured of (a) a capsule endoscope, (b) a receiver device, and (c) an image analysis device. The present disclosure is directed to (a) a capsule endoscope in the capsule endoscope system.

Figure 1:
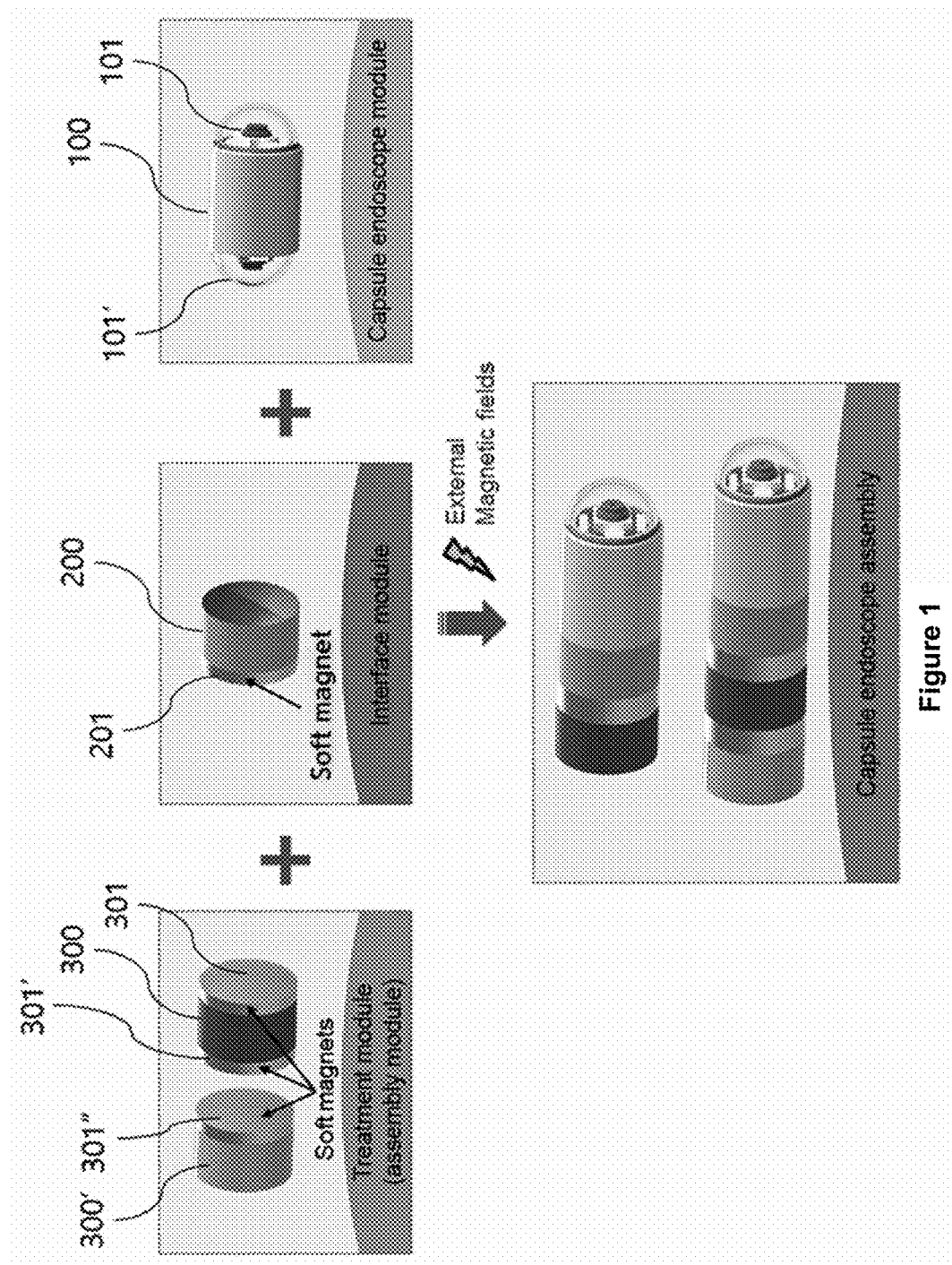
FIG. 1 shows respective modules configuring a capsule endoscope assembly according to an aspect of the present disclosure before and after assembly.

FIG. 1 shows respective modules configuring a capsule endoscope assembly according to an aspect of the present disclosure before and after assembly.

As shown in FIG. 1, the capsule endoscope assembly according to an aspect of the present disclosure is modularized into respective components. For example, the capsule endoscope assembly of the present disclosure is configured of a capsule endoscope module 100, an interface module 200, and a treatment module 300.

The capsule endoscope module 100 has a camera at either one or both ends thereof and can photograph the outside. The capsule endoscope module 100 includes a permanent magnet inside. Therefore, the capsule endoscope module 100 is an active capsule endoscope, the operation of which can be controlled by application of a magnetic field from the outside. The capsule endoscope module 100 has a camera at either one or both ends thereof, so that a user can monitor in real time an image of the inside of a digestive organ of a subject.

The capsule endoscope module of the present disclosure may be in the shape of an easy-to-swallow small-sized pill, but is not limited thereto.

The capsule endoscope module of the present disclosure may have a size of 5 to 20 mm×15 to 40 mm, for example, 10 to 18 mm×20 to 35 mm, but is not limited thereto.

The capsule endoscope module of the present disclosure may include an LED-containing optical device, an image sensor, a battery, a communication device, and the like, but is not limited thereto.

The capsule endoscope module of the present disclosure can photograph several to tens of still images or operation images per second, and transmit data in real time to a receiver device possessed by a patient or a receiver device of an examiner (e.g., a doctor). The examiner can store the received image data as still pictures or videos as needed.

A lens of the camera included in the capsule endoscope module of the present disclosure preferably has as wide an angle as possible. However, the capsule endoscope of the present disclosure is an active capsule endoscope capable of controlling the position and operation thereof, and thus a photographing (angle) range of at least 80° or more is sufficient, and for example, a photographing range of 100 degrees causes no problem. Conventional passive capsule endoscopes need to be implemented so as to photograph an image in the range of at least 140 degrees.

Conventional passive capsule endoscope modules proceed only by the peristalsis of the intestine and photograph the inside of digestive tracts. Therefore, under the vigorous peristalsis of the intestine, the capsule endoscopes proceed promptly, failing to photograph a site of interest, and under the extremely slow or stationary peristalsis of the intestine, the capsule endoscopes repeatedly photograph unnecessary still images, causing power consumption.

The capsule endoscope module of the present disclosure forms a magnetic field outside or inside the human body by including a permanent magnet or an electromagnet, so that the position and posture of the capsule endoscope module can be controlled in real time. Thus, according to the present disclosure, an examiner can actively control the position and posture of the capsule endoscope module of the present disclosure without relying on the peristalsis of the intestine of a subject.

The capsule endoscope module of the present disclosure includes a permanent magnet or an electromagnet, so the position of the capsule endoscope module can be determined by detecting a magnetic field emitted from the capsule endoscope module.

In another embodiment of the present disclosure, the capsule endoscope module of the present disclosure may include an RF module.

In the present disclosure, the RF module can convert image data into an RF signal and wirelessly transmit the RF signal to the outside of the human body.

When the capsule endoscope module of the present disclosure includes the RF module, the position of the capsule endoscope module can be determined by analyzing the RF signal of the RF module.

In the present disclosure, the interface module 200 is disposed between the active capsule endoscope module and the treatment module 300 to function to connect the two to each other, and a portion or the entirety of the interface contains a soft magnetic material. When a portion of the interface contains a soft magnetic material 201, the soft magnetic material is contained in either one or both sides of the interface module. In addition, the interface module 200 is configured in a hollow cylindrical shape so that a hole is formed in the center of the inside of the interface module 200 so that the field of view of the capsule endoscope 100 can be secured when the interface module 200 is coupled to the capsule endoscope. Therefore, the capsule endoscope module 100 and the interface module 200 of the present disclosure in an assembled state can photograph images in both directions even while moving along digestive organs of a subject, and can be assembled with the treatment module 200 while checking the position of the treatment module 300.

In one embodiment of the present disclosure, the capsule endoscope assembly of the present disclosure may include at least one capsule endoscope module, at least one interface module, and at least one treatment module.

In a specific embodiment of the present disclosure, a portion or the entirety of the treatment module of the present disclosure contains a soft magnetic material. When a portion of the treatment module contains a soft magnetic material, the soft magnetic material is contained in either one side 301 or both sides 301 and 301' of the treatment module.

When both sides of the treatment module contain a soft magnetic material, the connection (assembly) of treatment modules is attained by attractive force between a soft magnet 301" of one treatment module and a soft magnet 301' of another treatment module upon the application of an external magnetic field. Therefore, an additional interface is not needed when two or more treatment modules are connected (see FIG. 1).

In the present disclosure, the treatment module 300 includes therein devices for various types of diagnosis and treatment, such as diagnosis, treatment, and biopsy, and a portion or the entirety of the module, excluding the diagnostic or treatment device configurations within the module, contains a soft magnetic material.

That is, in one embodiment of the present disclosure, the treatment module 300 may include diagnostic device configurations, such as a pH sensing device, a pressure sensing device, a viscosity sensing device, and an impedance sensing device, but is not limited thereto.

In a specific embodiment of the present disclosure, the pH sensing device of the present disclosure may include a pH sensing unit for measuring the pH of a digestive fluid in contact with the capsule endoscope assembly, a pH measurement information output unit, and a data transmission unit.

In a specific embodiment of the present disclosure, the pressure sensing device of the present disclosure may include a pressure sensing unit, a pressure measurement information output unit, and a data transmission unit. The pressure sensing unit may be used to analyze the hardness of a tissue and distinguish between cancer tissues and ordinary tissues by measuring the pressure that is input when a pressure measurement probe comes into contact with a lesion site or tissue site, the pressure of which is to be measured.

In a specific embodiment of the present disclosure, the viscosity sensing device of the present disclosure may include a viscosity sensing unit, a viscosity measurement information output unit, and a data transmission unit. The viscosity sensing unit may be used to measure the viscosity of the blood.

In a specific embodiment of the present disclosure, the impedance sensing device of the present disclosure may include an impedance sensing unit including an electrode pair, an impedance information output unit, and a data transmission unit. The impedance sensing device may be used to distinguish cancer tissue and ordinary tissue by allowing the current to flow through a lesion site or tissue site to measure the impedance.

In another embodiment of the present disclosure, the treatment devices included in the treatment module of the present disclosure may include a drug delivery device, a tattooing device, an endoscopic clip, and the like, but are not limited thereto.

Examples of the drug that is delivered by the drug delivery device of the present disclosure include hemostatic agents/adhesives, wound coverings, photodynamic/photothermal treatment agents (photosensitizers), or anti-inflammatory agents, for topical application to lesions inside digestive organs, but are not limited thereto.

The form of delivery of the drug according to the present disclosure includes microneedles, microparticles, nanoparticles, liposomes, gels, microemulsions, nanocapsules, polymer micelles, and the like, but is not limited thereto.

The tattooing device of the present disclosure is configured for an examiner to mark a lesion site to be marked in a digestive organ of a subject, and can mark the position to be marked by containing a biocompatible dye.

In another embodiment of the present disclosure, the treatment module of the present disclosure may include a biopsy device. The biopsy device is a tissue biopsy device for collecting a tissue of a lesion site or a liquid biopsy device for collecting a liquid (digestive fluid or blood) in a digestive organ. The tissue biopsy device may include a blade for tissue collection and a storage unit for the collected tissue.

The liquid biopsy device of the present disclosure may be used to analyze factors that affect the health status of a subject, for example, the types and proportions of intestinal microorganisms, the pH in the digestive fluid, hormones, the presence or absence of inflammatory cells/blood, electrolyte distribution, or the like, after the collection of the digestive fluid/blood.

Figure 2:
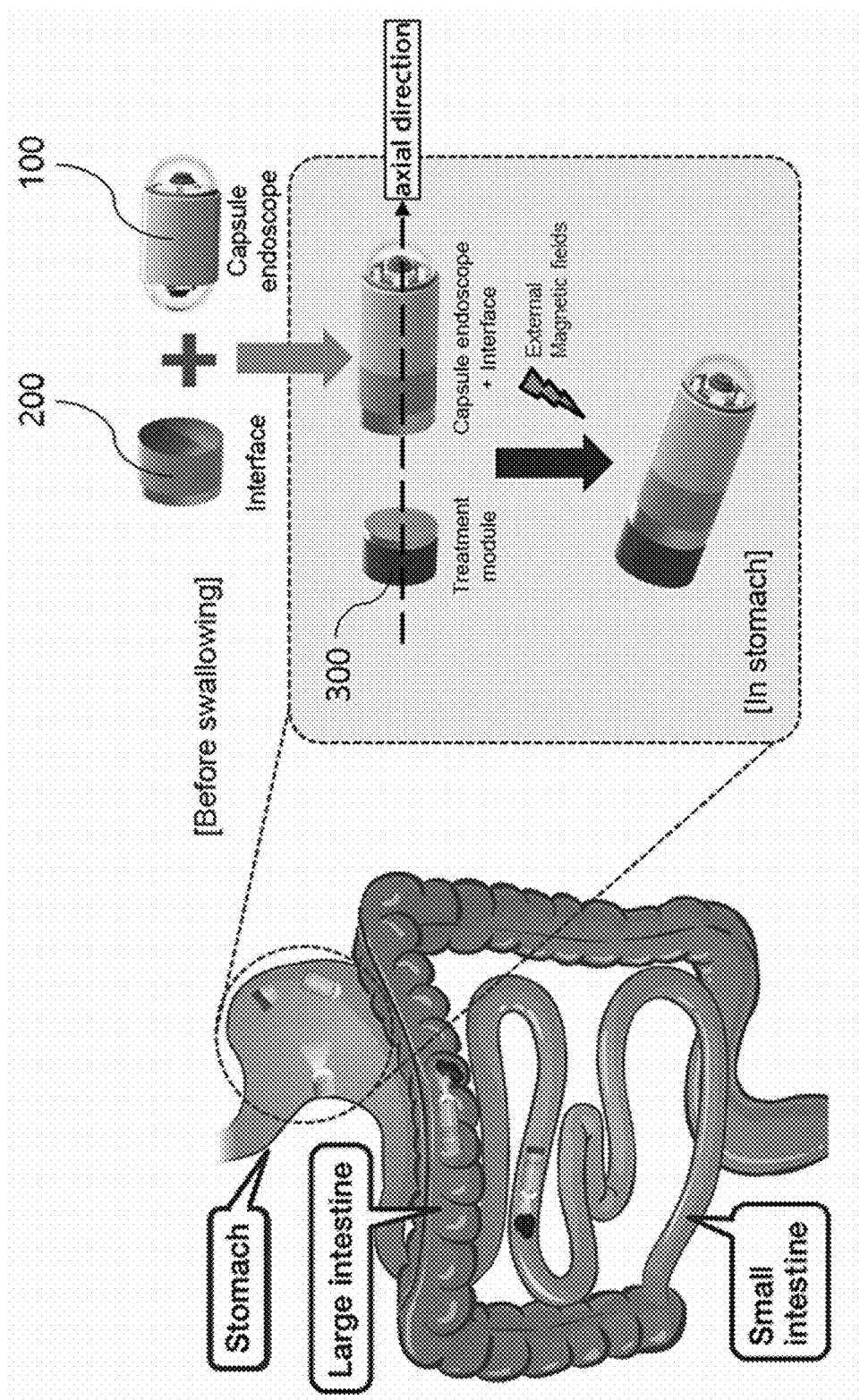
FIG. 2 shows a first scenario in which the modularized capsule endoscope assembly of the present disclosure is assembled in the gastrointestinal tract of a subject.

FIG. 2 shows a first scenario in which the modularized capsule endoscope assembly of the present disclosure is assembled in the gastrointestinal tract of a subject.

Referring to FIG. 2, the active capsule endoscope module 100, the interface module 200, and the treatment module 300 having various functions, which configure the capsule endoscope assembly according to an aspect of the present disclosure, are assembled in the gastrointestinal tract of a subject as follows.

i) First, the capsule endoscope 100 is coupled to the interface module 200 before a subject swallows the capsule endoscope 100.

ii) After the subject is made to swallow the active capsule endoscope 100 coupled to the interface module 200, the subject is made to swallow the treatment module 300, separately. (The order of i) and ii) makes no difference.)

iii) By using an external magnetic field generator (electromagnetic actuation system), the capsule endoscope module 100 is moved to the vicinity of the separately swallowed treatment module 300 while an image from the active capsule endoscope 100 coupled to the interface module 200 is checked in real time (The field of view in both directions is secured through the central hole of the interface).

iv) By using the external magnetic field generator, a magnetic field is generated in a direction (the axial direction of the assembly) for coupling the capsule endoscope module 100—interface module 200 system and the treatment module 300.

v) Through the generated external magnetic field, the capsule endoscope module 100—the interface module 200 and the treatment module 300 coupled to the capsule endoscope 100 are magnetized in the direction of the magnetic field, wherein the capsule endoscope module 100—interface module 200 system are assembled by the attractive force generated between the interface module 200 and the treatment module 300.

Figure 3:
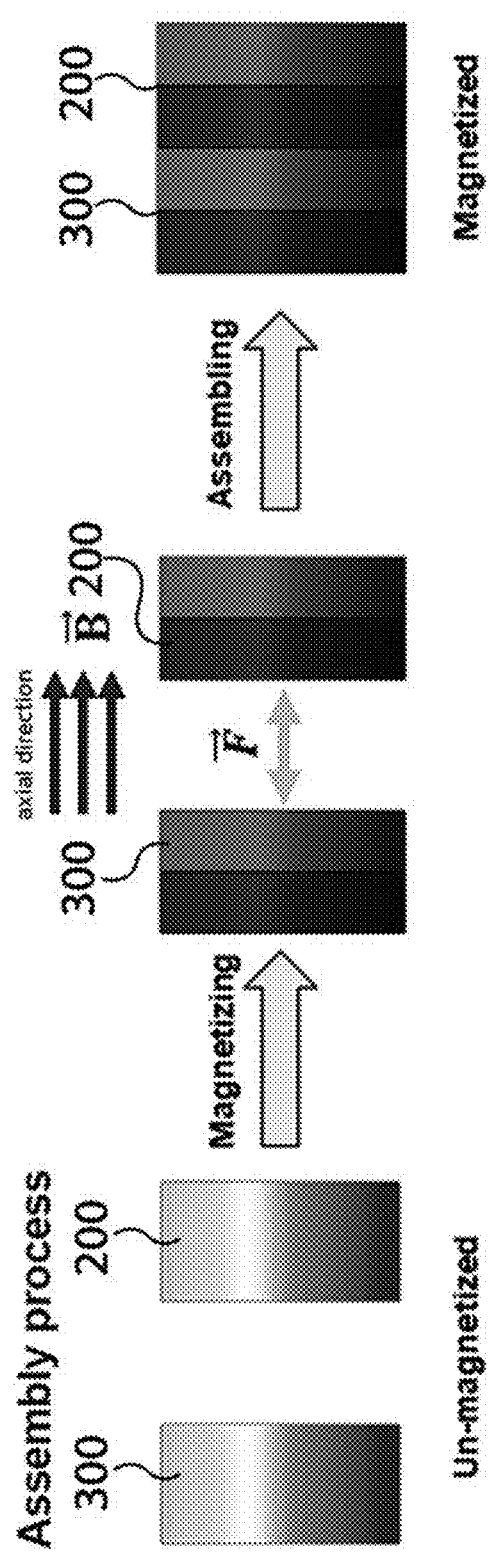
FIG. 3 shows a principle in which respective modules configuring the capsule endoscope assembly of the present disclosure are assembled.

FIG. 3 shows a principle in which the respective modules configuring the modularized capsule endoscope assembly of the present disclosure are assembled.

The interface module 200 and the treatment module 300 configuring the capsule endoscope assembly of the present disclosure contain a soft magnetic material. The soft magnet refers to a magnet that is strongly magnetized along the direction of an external magnetic field under even a small external magnetic field and has a small residual magnetization. That is, the soft magnet does not exhibit magnetism by itself due to the small residual magnetization in the absence of a magnetic field outside.

Referring to FIG. 3, the interface module 200 and the treatment module 300 including soft magnets in the present disclosure are magnetized in a length direction when a magnetic field is applied in the axial direction (or length direction) of the assembly as shown in FIG. 3 by using an external magnetic field generator (an external actuation system for controlling the capsule endoscope). Therefore, the attractive force is generated between the soft magnets included in the interface module 200 and the treatment module 300, and as a result, the respective modules are coupled to each other to configure the assembly.

In addition, during the driving (movement and operation control) of the capsule endoscope assembly in which the respective modules are coupled, the application of an external magnetic field in the axial direction (or length direction) of the capsule endoscope assembly can easily move the capsule endoscope assembly and control the operation thereof in a state in which all the respective modules are coupled.

Figure 4:
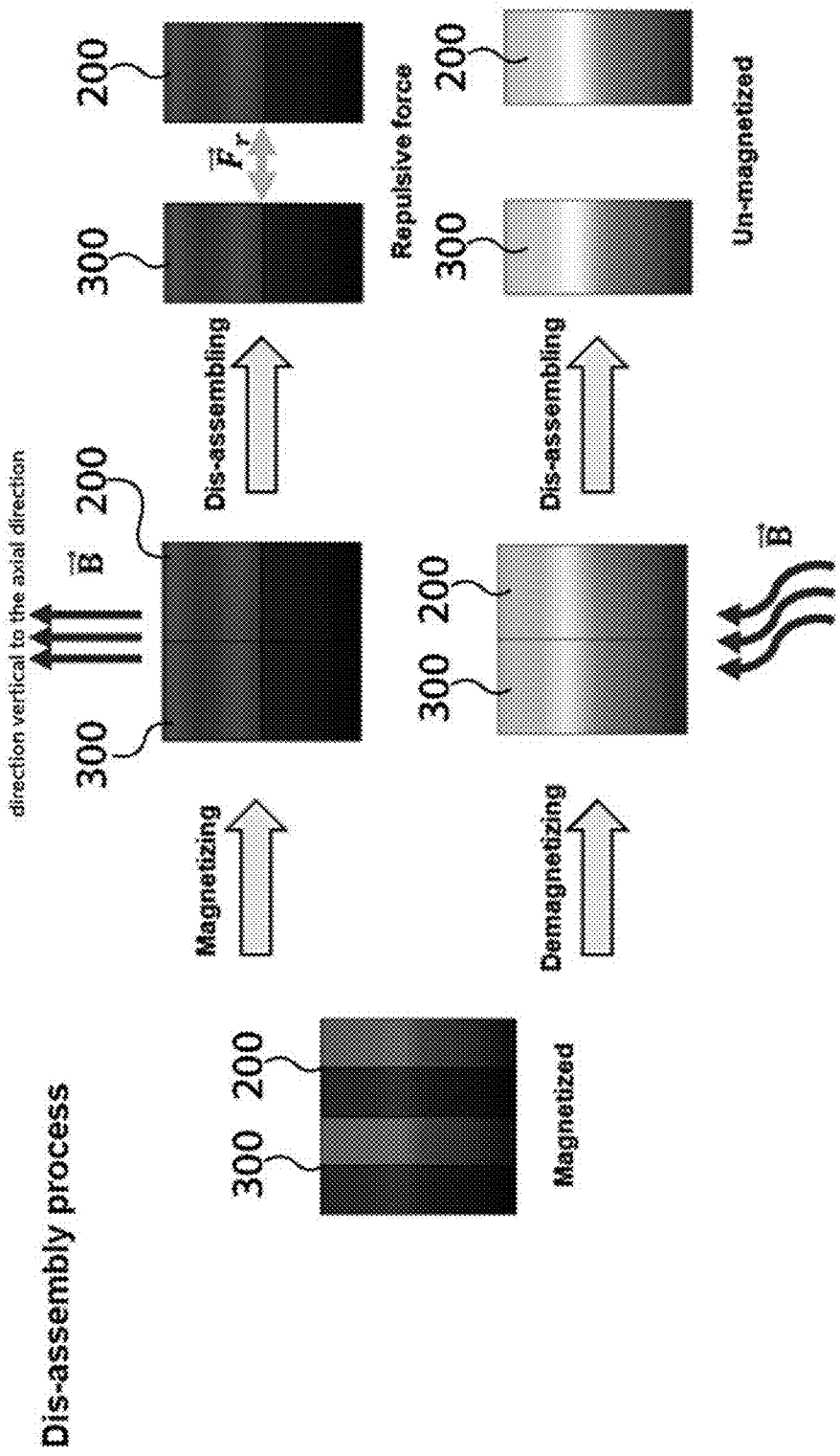
FIG. 4 shows a principle in which respective modules configuring the modularized capsule endoscope assembly of the present disclosure are disassembled.

FIG. 4 shows a principle in which the respective modules configuring the modularized capsule endoscope assembly of the present disclosure are disassembled.

The modules configuring the capsule endoscope assembly of the present disclosure need to be separated according to the diagnosis, treatment method, and purpose. For instance, when the treatment module 300 includes a device that is developed for long-term monitoring, such as an implant-type sensor inserted into digestive organs, the treatment module 300, the capsule endoscope module 100, and the interface module 200 need to be separated and only the treatment module 300 needs to remain in the digestive organs.

Referring to FIG. 4, there are two mechanisms for separating the respective modules of the capsule endoscope assembly of the present disclosure.

i) The first mechanism is to use the repulsive force between the interface module 200 and the treatment module 300 by changing the magnetization direction of the soft magnets included in the interface module 200 and the treatment module 300 through an external magnetic field generator, and ii) the second mechanism is to demagnetize the soft magnets.

Specifically, according to the first mechanism, the direction of the magnetic field applied to the capsule endoscope assembly of the present disclosure in the axial direction (or the length direction) is changed to a direction vertical to the axial direction. Due to the change in direction of the magnetic field, the magnetization direction of the soft magnets included in the interface module 200 and the treatment module 300 is changed to a direction perpendicular to the length direction of the assembly. Therefore, the repulsive force is generated between the soft magnets included in the interface module 200 and the treatment module 300, and as a result, the respective modules are separated from each other.

According to the second mechanism, the magnetized soft magnets are demagnetized. Through the removal of the magnetic field applied from the outside to the soft magnets magnetized in the length direction of the assembly, the attractive force between the soft magnets included in the interface module 200 and the treatment module 300 is eliminated, and thus the modules are separated. Specifically, the removal of the magnetic field can be attained by reversing the direction of the applied magnetic field, like a sine wave form. The removal of the magnetic field results in the demagnetization of the magnetized soft magnets. That is, when the direction of the magnetic field applied to the assembly is reversed, the atomic magnetic moments of the soft magnets, which have been aligned in a predetermined direction by an external magnetic field, are converted into a form that has irregular atomic magnetic moments, as before magnetization, and thus the attractive force between the soft magnets is lost.

The magnetized state of a soft magnet and a paramagnet refers to a state in which the atomic magnetic moments inside the soft magnet and the paramagnet are aligned in the predetermined direction. On the other hand, the state in which the magnetism of the soft magnet and the paramagnet is eliminated (demagnetized) refers to a state in which the internal atomic magnetic moments are irregularly aligned.

In accordance with another aspect of the present disclosure, there is provided a capsule endoscope system including:

a capsule endoscope assembly including the capsule endoscope module 100, the treatment module 300, and the interface module 200;

a second capsule endoscope module 400 having a camera at one end thereof to photograph the outside; and a fixing device 500 including a permanent magnet and configured to fix the second endoscope module onto the inner wall of a digestive organ outside the body of a subject.

Figure 5:
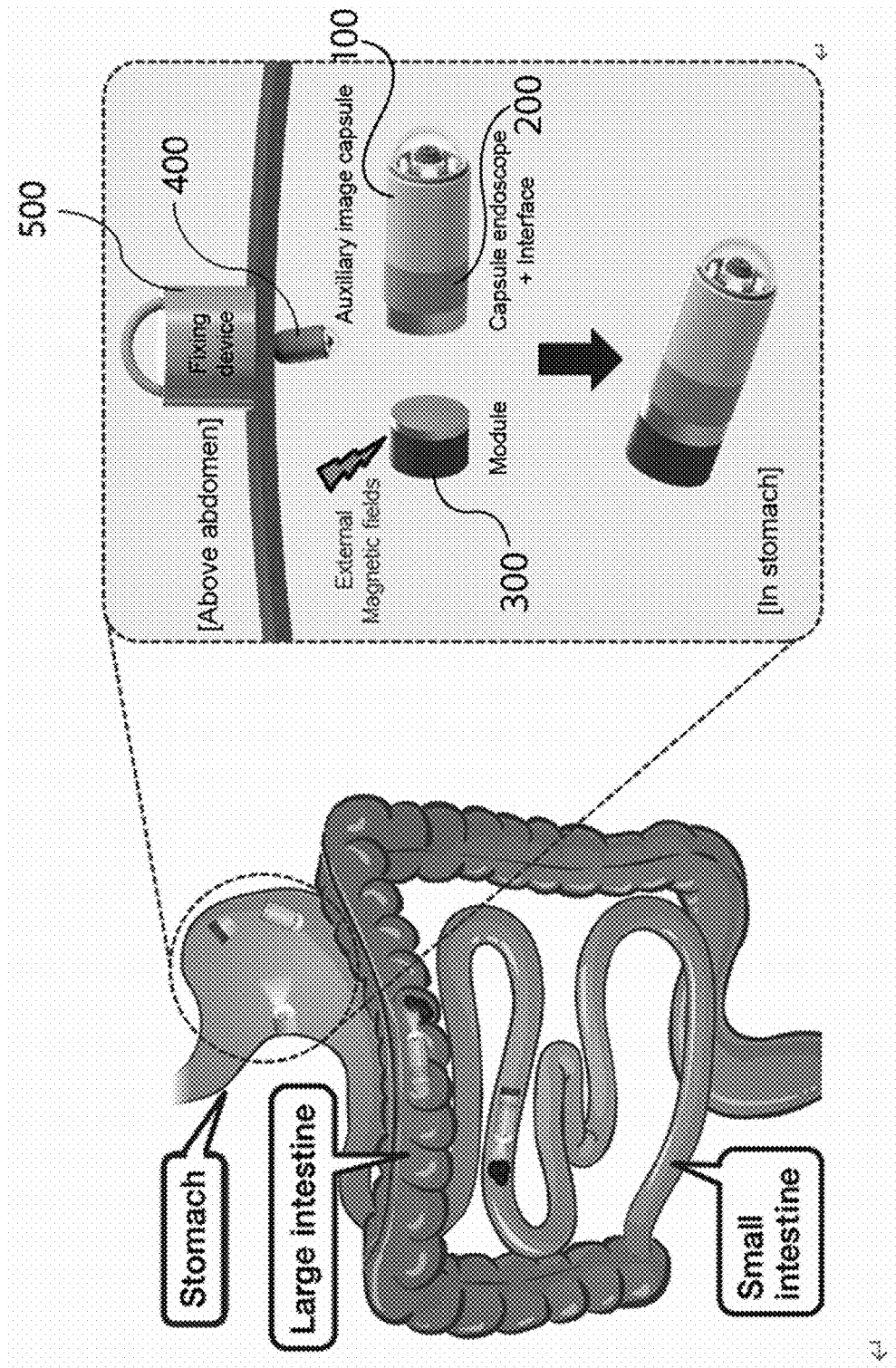
FIG. 5 shows a second scenario in which a capsule endoscope system according to another aspect of the present disclosure is assembled in the gastrointestinal tract of a subject.

FIG. 5 shows a second scenario in which a capsule endoscope system according to another aspect of the present disclosure is assembled in the gastrointestinal tract of a subject.

Referring to FIG. 5, the capsule endoscope system according to another aspect of the present disclosure includes the active capsule endoscope module (100 or auxiliary image capsule), the interface module 200, and the treatment module 300, which are described above, and further includes a second capsule endoscope module 400 and a fixing device 500 for securing an auxiliary image. The second capsule endoscope module 400 is used for securing the field of view toward the capsule endoscope module 100, the interface module 200, and the treatment module 300 while the respective modules are assembled. The second capsule endoscope module 400 is fixed onto the inner wall of the gastrointestinal tract by the action of the fixing device located outside the body (e.g., on the abdomen) of the subject.

Figure 6:
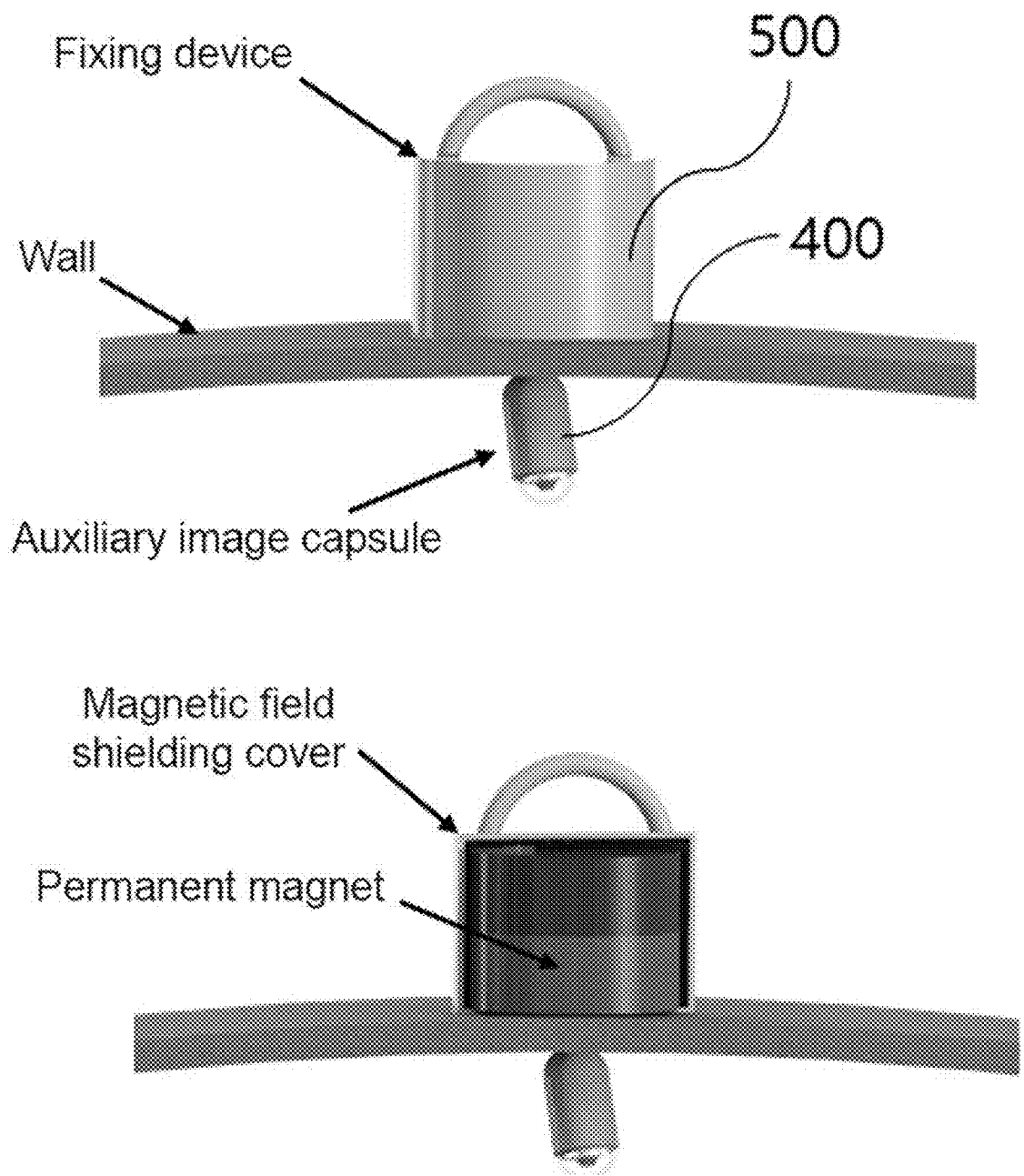
FIG. 6 shows a second capsule endoscope and a fixing device, for securing an auxiliary image, which configure the capsule endoscope system of the present disclosure.

FIG. 6 shows the second capsule endoscope 400 and the fixing device 500, for securing an auxiliary image, which configure the capsule endoscope system of the present disclosure.

In an embodiment of the present disclosure, the second capsule endoscope 400 includes a permanent magnet therein. The fixing device 500 includes a permanent magnet therein so that the second capsule endoscope 400 can be fixed onto the stomach wall.

Referring to FIGS. 5 and 6, a procedure in which the capsule endoscope system of the present disclosure is assembled in a digestive organ of a subject will be described as follows:

i) First, in order to secure the field of view while the capsule endoscope module 100, the interface module 200, and the treatment module 300 of the present disclosure are assembled, the second capsule endoscope (400 or an auxiliary image capsule) is swallowed by a subject.

ii) Thereafter, the second capsule endoscope module 400 of the present disclosure is fixed onto the stomach wall by placing the fixing device 500 on the upper abdomen.

iii) The assembly order thereafter is the same as the assembly procedure of the above-described capsule endoscope assembly of the present disclosure. However, in the capsule endoscope system of the present disclosure, the field of view for assembly is not secured by using a two-directional camera of the capsule endoscope module 100, but the field of view is secured through the images transmitted from the second capsule endoscope module 400 fixed onto the stomach wall.

Figure 7:
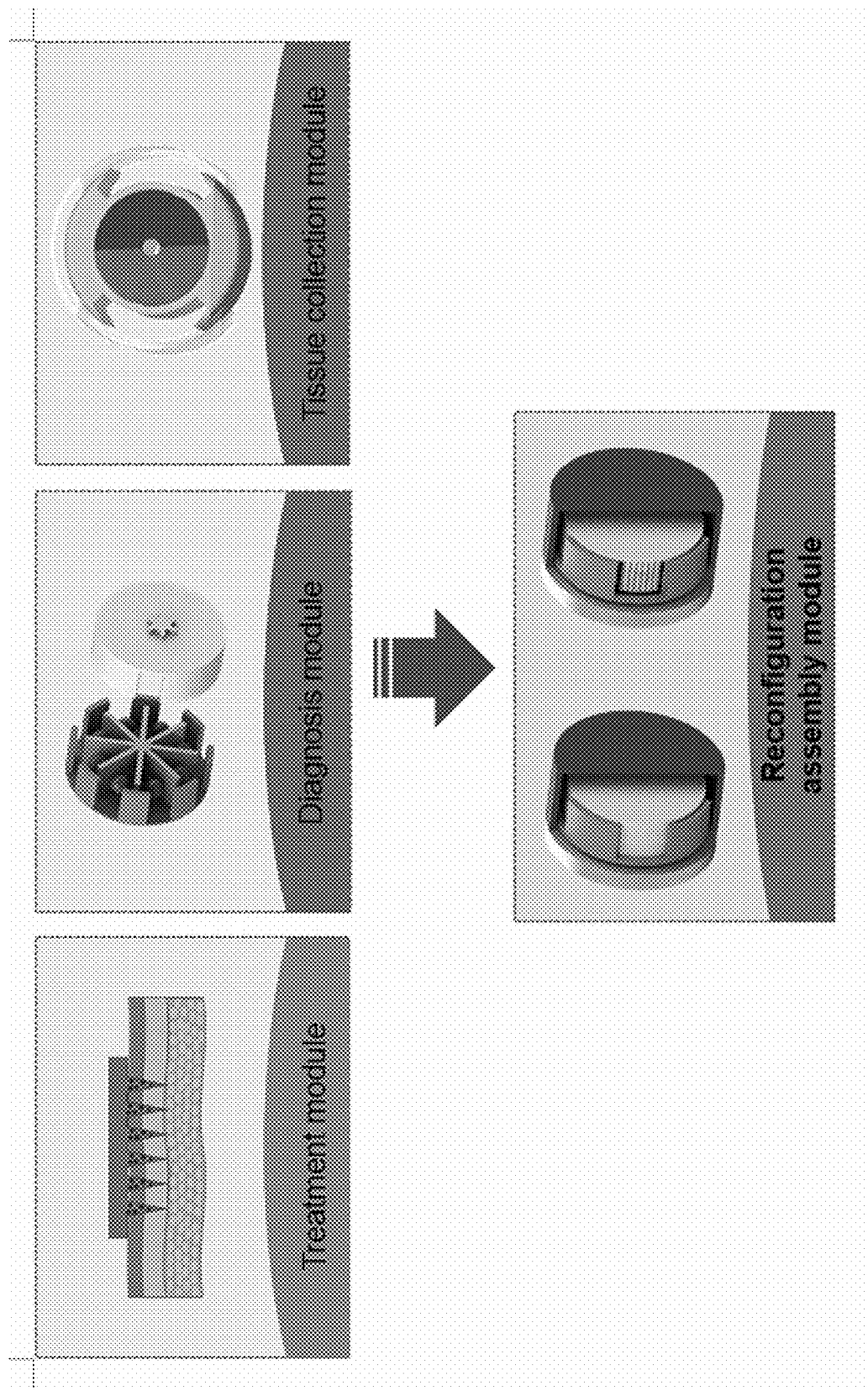
FIG. 7 shows that various diagnostic and treatment functions can be mounted by modularizing various diagnostic and/or treatment devices and including the devices in a capsule endoscope assembly of the present disclosure.

FIG. 7 shows that various diagnostic and treatment functions can be mounted by modularizing various diagnostic and/or treatment devices and including the devices in a capsule endoscope assembly of the present disclosure.

Since the configuration of the treatment module is the same as that of the capsule endoscope assembly according to a first embodiment of the present disclosure, the description of overlapping contents therebetween is omitted in order to avoid excessive complexity of the present specification.

FIGS. 8A to 8E show the assembly and disassembly test results of the capsule endoscope assembly of the present disclosure.

Figure 8A:
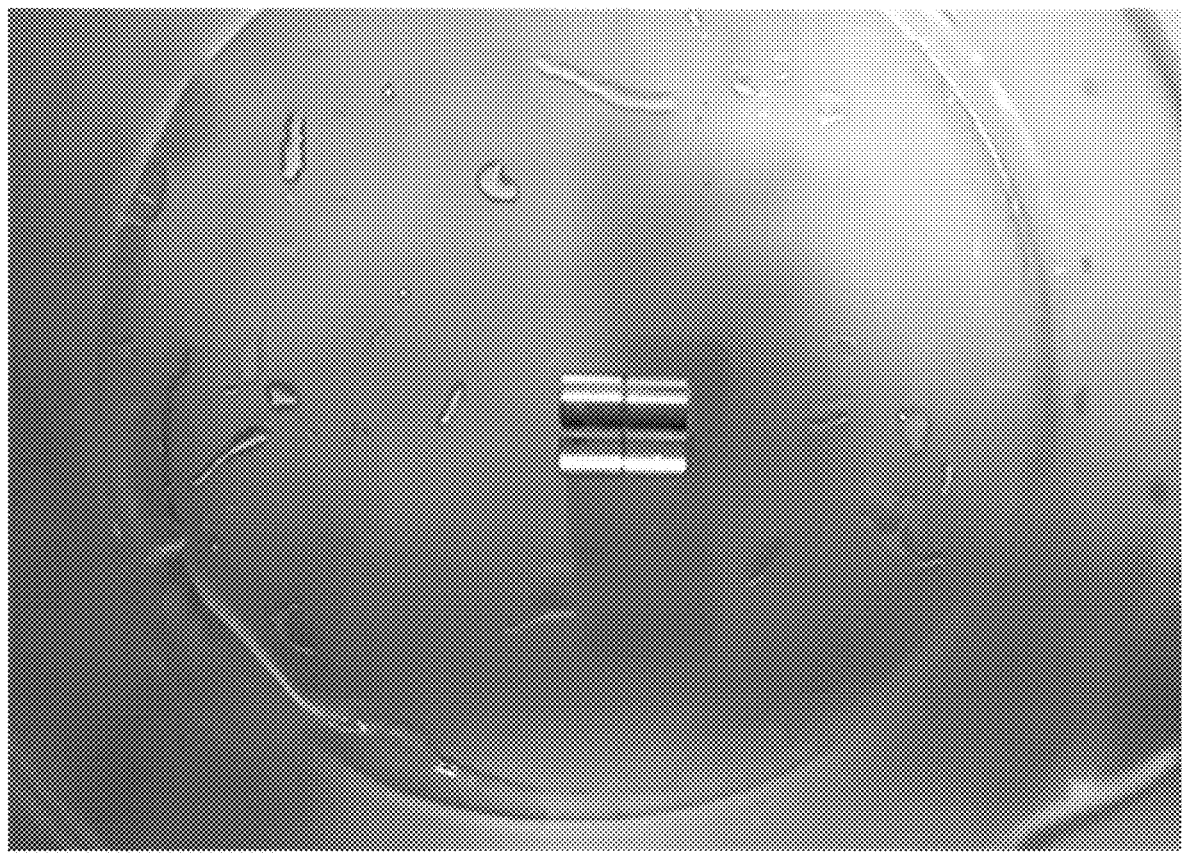
FIG. 8A shows the initial position of the capsule endoscope assembly of the present disclosure in the assembly and disassembly analysis results thereof.
Figure 8B:
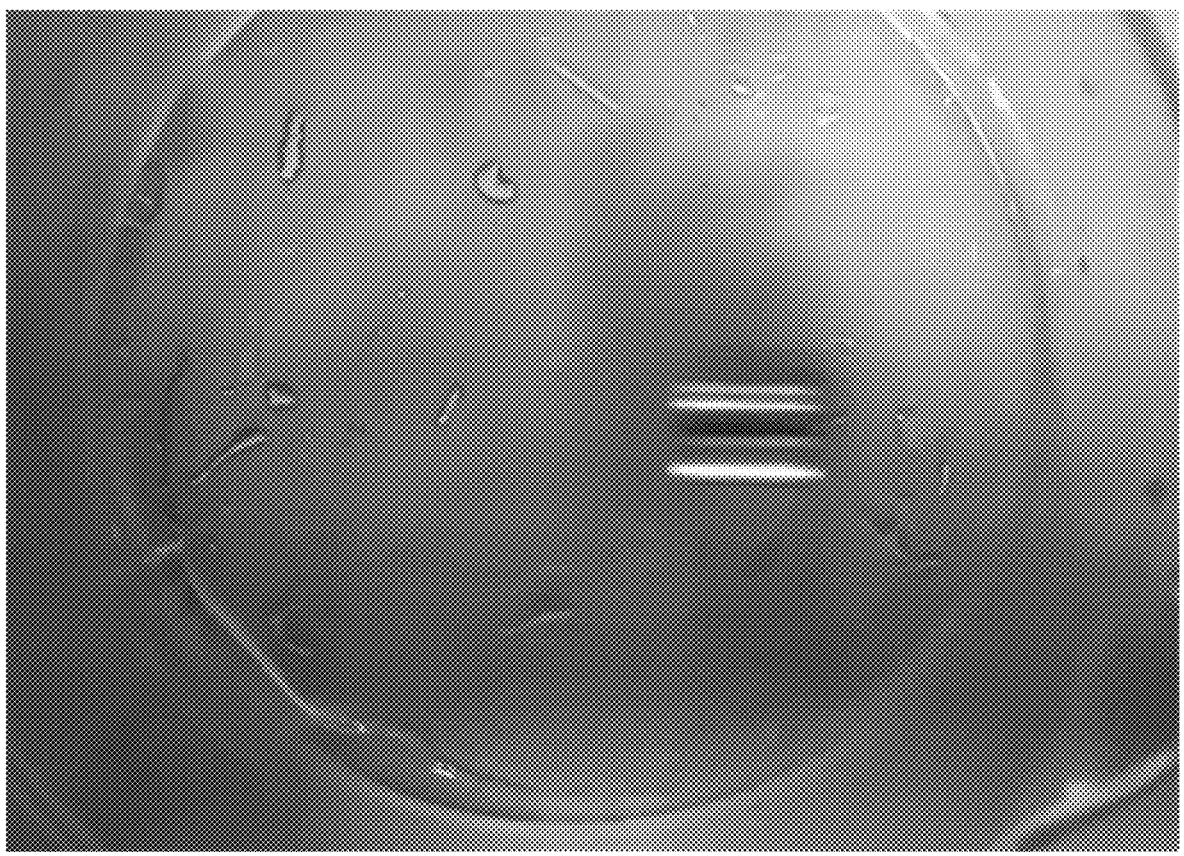
FIG. 8B shows the rightward movement of the capsule endoscope assembly of the present disclosure in the assembly and disassembly analysis results thereof.
Figure 8C:
FIG. 8C shows the leftward movement of the capsule endoscope assembly of the present disclosure in the assembly and disassembly analysis results thereof.
Figure 8D:
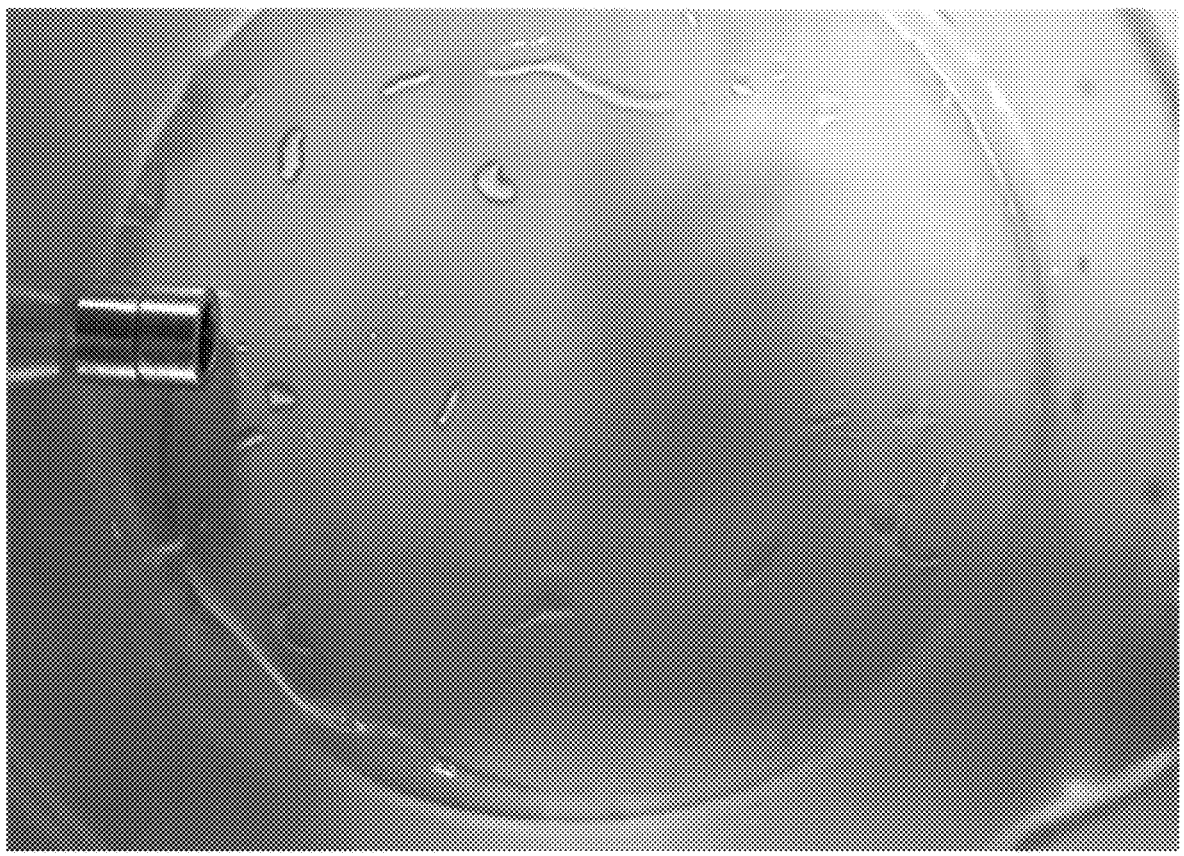
FIG. 8D shows the arrival at the corresponding position of the capsule endoscope assembly of the present disclosure in the assembly and disassembly analysis results thereof.
Figure 8E:
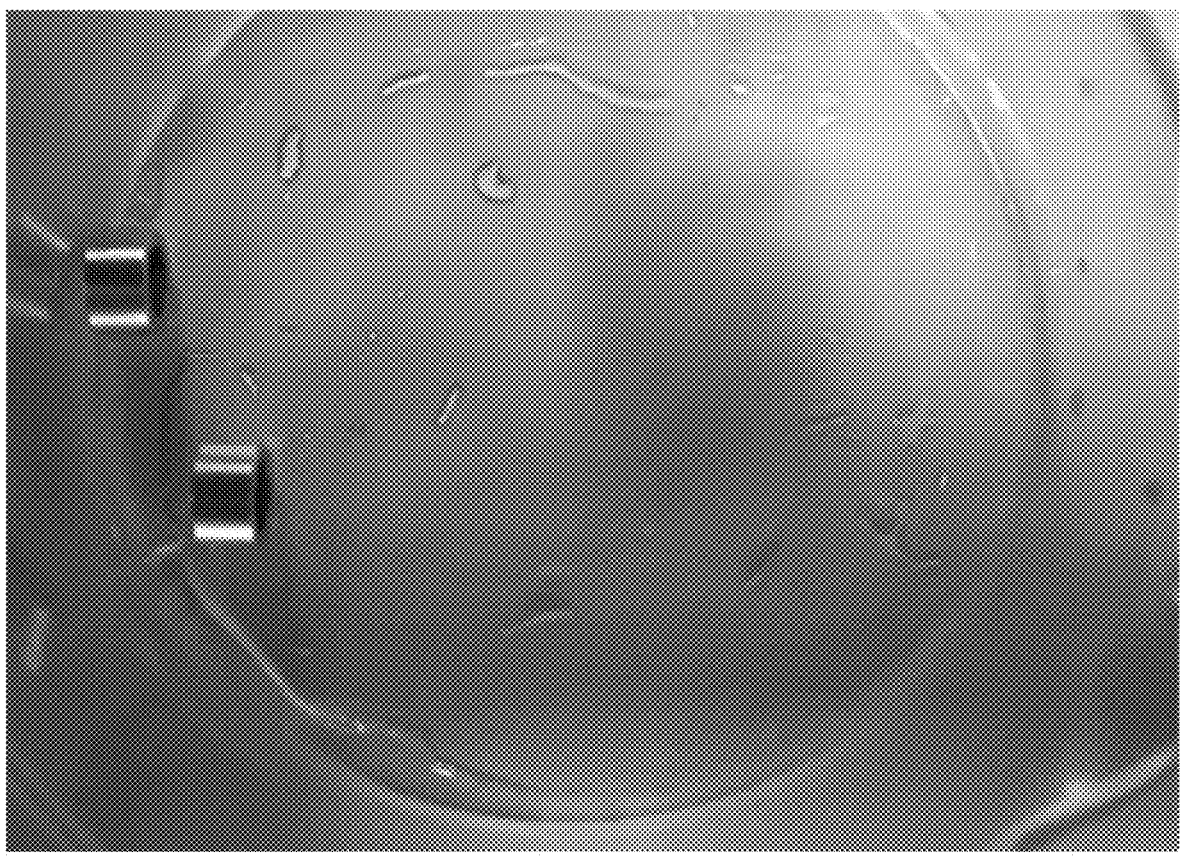
FIG. 8E shows the disassembled state of the capsule endoscope assembly of the present disclosure in the assembly and disassembly analysis results thereof.

FIGS. 8A to 8E show the results of simulating the assembly, control, and disassembly of two modules configuring the capsule endoscope assembly of the present disclosure. As shown in FIGS. 8A to 8D, the position of the capsule endoscope assembly of the present disclosure can be actively controlled by applying an external magnetic field to the capsule endoscope assembly. As shown in FIG. 8E, the coupled modules configuring the assembly can be separated by changing the direction of the magnetic field.

As described above, the capsule endoscope of the present disclosure includes a permanent magnet inside, and thus the capsule endoscope can be actively controlled through the application of a magnetic field.

In addition, the capsule endoscope assembly/system of the present disclosure can load various functions that could be achieved only through conventional typical endoscopes, by modularizing capsule endoscopes, configuring the assembly/system, and various types of devices for diagnosis and treatment according to diagnosis and treatment purposes.

In addition, the respective modules configuring the assembly of the present disclosure contain a permanent magnet or a soft magnetic material, so that the respective modules can be freely assembled or disassembled in a digestive organ of a subject through the application of a magnetic field. Furthermore, the assembly can be easily controlled according to the intention of the capsule operator.

EXPLANATION OF REFERENCE NUMERALS

100: Capsule endoscope module
101, 101': Camera
200: Interface module
201, 301, 301'301": Soft magnet
300, 300': Treatment module
400: Second capsule endoscope module
500: Fixing device

INDUSTRIAL APPLICABILITY

The present disclosure relates to a modular capsule endoscope reconfigurable in a digestive organ.

What is claimed is:

1. A capsule endoscope assembly capable of being assembled or disassembled in a digestive organ of a subject, the capsule endoscope assembly comprising:
a capsule endoscope module having a camera at either one or both ends thereof to photograph an outside view of the capsule endoscope assembly;
a treatment module for treatment, diagnosis, or biopsy of a lesion site of the subject; and
an interface module coupled to the capsule endoscope and the treatment module therebetween and comprising a soft magnet,
wherein the interface module has a hollow cylindrical shape so that a hole is formed in the center of the interface module not to obstruct the view of the camera.

2. The capsule endoscope assembly of claim 1, wherein the capsule endoscope module comprises a permanent magnet.

3. The capsule endoscope assembly of claim 1, wherein the capsule endoscope assembly is configured to be assembled by an attractive force between the interface module and the treatment module, which is generated by the magnetization of the soft magnet included in the interface module when an external magnetic field is applied in parallel to an axial direction of the endoscope assembly.

4. The capsule endoscope assembly of claim 3, wherein the soft magnet is selected from the group consisting of pure iron, electromagnetic soft iron, silicon steel, permalloy (Ni-Fe bases), Co-Fe-based alloys, sendust (Fe-Al-Si bases), Mn-Zn-based ferrites, Ni-Zn-based ferrites, Fe-based amorphous alloys, Co-based amorphous alloys, Fe-based thin films and multilayer films, Co-based thin films and multilayer films, and Ni-based thin films and multilayer films.

5. The capsule endoscope assembly of claim 1, wherein the capsule endoscope assembly is configured to be disassembled by an elimination of the attractive force between the interface module and the treatment module through a removal of an external magnetic field, or by a repulsive force between the interface module and the treatment module, which is generated when an external magnetic field is applied in a direction vertical to an axial direction of the capsule endoscope assembly.

6. The capsule endoscope assembly of claim 1, wherein the treatment module comprises a diagnostic device selected from the group consisting of a pH sensing device, a pressure sensing device, a viscosity sensing device, and an impedance sensing device.

7. The capsule endoscope assembly of claim 1, wherein the treatment module comprises a treatment device selected from the group consisting of a drug delivery device, a tattooing device, and an endoscopic clip.

8. The capsule endoscope assembly of claim 1, wherein the treatment module includes a tissue biopsy device or a liquid biopsy device.

9. A capsule endoscope system comprising:
the capsule endoscope assembly of claim 1;
a second capsule endoscope module having a camera at one end thereof to photograph an outside view of the capsule endoscope assembly; and
a fixing device comprising a permanent magnet and configured to fix the second endoscope module onto the inner wall of a digestive organ wherein the fixing device is placed outside a body of a subject.

* * * * *